United States Patent
Braun et al.

(10) Patent No.: US 9,243,094 B2
(45) Date of Patent: *Jan. 26, 2016

(54) THICKENING POLYMER FOR IONIC OIL PHASES FREE OF MONOMERS

(71) Applicants: Olivier Braun, Castres (FR); Jean-Noel Ollagnier, Castres (FR)

(72) Inventors: Olivier Braun, Castres (FR); Jean-Noel Ollagnier, Castres (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/564,446

(22) Filed: Dec. 9, 2014

(65) Prior Publication Data

US 2015/0094440 A1   Apr. 2, 2015

Related U.S. Application Data

(62) Division of application No. 13/701,641, filed as application No. PCT/FR2011/051275 on Jun. 6, 2011, now Pat. No. 8,937,101.

(30) Foreign Application Priority Data

Jun. 22, 2010   (FR) ...................................... 10 54933

(51) Int. Cl.

| | |
|---|---|
| C08F 220/18 | (2006.01) |
| A61K 8/81 | (2006.01) |
| A61K 8/86 | (2006.01) |
| A61K 47/32 | (2006.01) |
| C08F 290/06 | (2006.01) |
| C08F 222/10 | (2006.01) |
| A61Q 19/00 | (2006.01) |
| C08F 220/28 | (2006.01) |
| C08F 220/56 | (2006.01) |
| C08F 226/10 | (2006.01) |
| A61K 8/90 | (2006.01) |
| C08F 222/38 | (2006.01) |

(52) U.S. Cl.

CPC .............. *C08F 220/18* (2013.01); *A61K 8/8152* (2013.01); *A61K 8/86* (2013.01); *A61K 8/90* (2013.01); *A61K 47/32* (2013.01); *A61Q 19/00* (2013.01); *C08F 220/28* (2013.01); *C08F 220/56* (2013.01); *C08F 222/10* (2013.01); *C08F 222/38* (2013.01); *C08F 226/10* (2013.01); *C08F 290/062* (2013.01); *A61K 2800/10* (2013.01); *A61K 2800/48* (2013.01)

(58) Field of Classification Search

CPC .............. A61Q 19/00; A61K 2800/10; A61K 2800/48; C08F 220/18; C08F 220/28; C08F 220/56; C08F 226/10; C08F 290/062; C08F 222/38; C08F 222/10

See application file for complete search history.

(56) References Cited

U.S. PATENT DOCUMENTS

| | | | | |
|---|---|---|---|---|
| 3,249,545 | A | * | 5/1966 | Baurdoux et al. ............ 508/440 |
| 4,606,834 | A | * | 8/1986 | Hart et al. ..................... 508/471 |
| 5,318,995 | A | | 6/1994 | Mondet et al. |
| 5,736,125 | A | | 4/1998 | Morawsky et al. |
| 5,928,656 | A | | 7/1999 | Chaudhry et al. |
| 6,136,305 | A | | 10/2000 | Michel-Lecocu et al. |
| 6,197,287 | B1 | | 3/2001 | Mallo et al. |
| 6,375,959 | B1 | | 4/2002 | Mallo et al. |
| 7,101,928 | B1 | | 9/2006 | Bitler |
| 2008/0200590 | A1 | | 8/2008 | Schinabeck et al. |
| 2012/0157552 | A1 | | 6/2012 | Braun et al. |

FOREIGN PATENT DOCUMENTS

| | | |
|---|---|---|
| EP | 0 406 042 | 1/1991 |
| EP | 0 503 853 | 9/1992 |
| EP | 0 716 594 | 10/2001 |
| EP | 1 056 805 | 3/2004 |
| EP | 1 047 716 | 12/2006 |
| FR | 2 910 899 | 7/2008 |
| WO | 2006/002936 | 1/2006 |
| WO | 2006/064151 | 6/2006 |

* cited by examiner

*Primary Examiner* — Blessing M Bubara
(74) *Attorney, Agent, or Firm* — Young & Thompson

(57) ABSTRACT

A copolymer that includes for 100 mol %: a) more than 70 mol % and up to 99.9 mol % of hydrophobic monomer units (A) from stearyl methacrylate; and b) 0.1 mol % to 30 mol % of monomer units (B) from at least one monomer of a compound of formula (I) where R1 is a linear or branched alkyl radical comprising 12 to 22 carbon atoms, R2 is a hydrogen atom or a methyl radical, and n is an integer greater than or equal to 0 and lower than or equal to 30, wherein it is understood that said compound of formula (I) is not stearyl methacrylate. The invention also relates to a method for preparing and using same as a modifier of the rheology of the oil phase of a topical cosmetic, dermopharmaceutical, or pharmaceutical composition.

6 Claims, No Drawings

THICKENING POLYMER FOR IONIC OIL PHASES FREE OF MONOMERS

FIELD OF THE INVENTION

The present patent application relates to novel compounds for thickening oil phases, to the process for preparing same and to the application thereof as thickeners and/or emulsifiers for care products for the skin, the hair and the scalp, especially water-in-oil cosmetic, dermocosmetic, dermopharmaceutical or pharmaceutical emulsions.

BACKGROUND OF THE INVENTION

Synthetic thickening polymers in the form of inverse latices are described as being able to be used in the manufacture of topical compositions, in the European patent applications published under the numbers EP 0 716 594, EP 1 047 716, EP 1 056 805 and EP 0 503 853.

However, most of these thickeners are incapable of thickening oil phases.

The European patent application published under the number EP 0 406 042 discloses cosmetic compositions in the form of water-in-oil emulsions containing as thickener a polymer with a low proportion of units containing ionic groups, for instance the copolymer of N-dodecylacrylamide and of 2-acrylamido-2-methylpropanesulfonic acid (AMPS) in a 96.5/3.5 weight proportion or the copolymer of N-tert-butylacrylamide and of 2-acrylamido-2-methylpropanesulfonic acid in a 97.9/2.1 weight proportion. Such copolymers are difficult to use in the cosmetic industry since they must be neutralized before use, and since their dissolution in oils often requires the use of a cosolvent. Furthermore, their oil-thickening capacity is low.

It is for this reason that the only compounds known to date having this property are the copolymers sold under the name Intelimer, which are hydrophobic copolymers bearing long pendent alkyl chains, which crystallize under cold conditions to form clusters that bring about thickening of the medium. Such polymers of the type such as copolymers of an alkyl acrylate and of (meth)acrylic acid are described in the American patents published under the numbers U.S. Pat. No. 7,101,928 B1 and U.S. Pat. No. 5,736,125. However, the use of these products is not simple since the polymer needs to be dissolved in the oil under hot conditions, followed by cooling to bring about crystallization of the chains. Furthermore, they are by nature heat-sensitive and compositions thickened with a polymer of this type are difficult to market in hot countries.

This is why the Applicant has sought to develop novel polymers that are capable of thickening organic and oil phases, which do not have the drawbacks mentioned above.

SUMMARY OF THE INVENTION

The invention thus relates to copolymers based on stearyl methacrylate and also to a process for preparing the same in an apolar phase.

This copolymer is characterized in that it comprises, per 100 mol %:
a) more than 70 mol % and up to 99.9 mol % of hydrophobic monomer units (A) derived from stearyl methacrylate; and
b) from 0.1 mol % to 30 mol % of monomer units (B) derived from at least one monomer of a compound of formula (I):

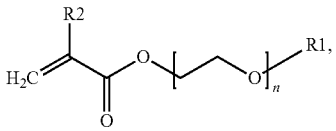

in which R1 represents a linear or branched alkyl radical comprising from 12 to 22 carbon atoms, R2 represents a hydrogen atom or a methyl radical and n is an integer greater than or equal to 0 and less than or equal to 30, it being understood that said compound of formula (I) is not stearyl methacrylate.

DETAILED DESCRIPTION OF THE INVENTION

In the preceding definition, the term "copolymer" denotes polymers of monomer units derived from at least two monomers of different chemical structure. The term "copolymers" thus also includes terpolymers, tetrapolymers and polymers of monomer units derived from more than four monomers of different chemical structure.

In formula (I) as defined previously, when the radical R1 represents a linear alkyl radical comprising from 12 to 22 carbon atoms, it is more particularly a radical chosen from dodecyl, tetradecyl, hexadecyl, octadecyl, eicosyl and docosyl radicals.

In formula (I) as defined previously, when the radical R1 represents a branched alkyl radical comprising from 12 to 22 carbon atoms, it may be a radical of formula:

in which m is an integer between 1 and 4 and n is an integer between 9 and 16; or a radical of formula:

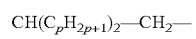

in which p is an integer between 5 and 10.

According to a particular aspect of the present invention, in formula (I) as defined previously, the radical R1 represents a linear alkyl radical chosen from dodecyl and docosanyl radicals.

According to one particular aspect of the present invention, in formula (I) as defined previously, the radical R2 represents a methyl radical.

According to one particular aspect of the present invention, in formula (I) as defined previously, n is greater than zero; it is more particularly greater than or equal to four and less than or equal to twenty five.

According to one particular aspect of the present invention, the monomer unit (B) is derived from pentacosaethoxylated behenyl methacrylate, which compound corresponds to formula (I) as defined previously, in which R1 represents a docosanyl radical, R2 represents a methyl radical and n is equal to 25. According to another particular aspect of the present invention, the monomer unit (B) is derived from tetraethoxylated lauryl methacrylate, which compound corresponds to formula (I) as defined previously, in which R1 represents a dodecyl radical, R2 represents a methyl radical and n is equal to 4.

According to another particular aspect, in the copolymer as defined previously, the mole ratio (A)/(B) is between 80/20 and 95/5.

A subject of the invention is more particularly the following copolymers:
- copolymer of stearyl methacrylate and of pentacosaethoxylated behenyl methacrylate [mole ratio (A)/(B) =95/5],
- copolymer of stearyl methacrylate and of pentacosaethoxylated behenyl methacrylate [mole ratio (A)/(B) =90/10],
- copolymer of stearyl methacrylate and of pentacosaethoxylated behenyl methacrylate [mole ratio (A)/(B) =85/15], or:
- copolymer of stearyl methacrylate and of pentacosaethoxylated behenyl methacrylate [mole ratio (A)/(B) =80/20].

A subject of the invention is also a copolymer as defined previously, characterized in that it also comprises, per 100 mol %, from 0.1 mol % to 30 mol % of monomer units (C) derived from at least one neutral monomer chosen from acrylamide, methacrylamide, N,N-dimethylacrylamide, N,N-diethylacrylamide, N-isopropylacrylamide, 2-hydroxyethyl acrylate, 2,3-dihydroxypropyl acrylate, 2-hydroxyethyl methacrylate, 2,3-dihydroxypropyl methacrylate and N-vinylpyrrolidone and more particularly N,N-dimethylacrylamide or N,N-diethylacrylamide.

According to one particular mode, a subject of the invention is a copolymer as defined previously comprising, per 100 mol %:
a) from 80 mol % to 95 mol % of hydrophobic monomer units (A);
b) from 2.5 mol % to 10 mol % of monomer units (B); and
c) from 2.5 mol % to 10 mol % of monomer units (C); and
more particularly the following copolymers:
- terpolymer of stearyl methacrylate, pentacosaethoxylated behenyl methacrylate and N,N-dimethylacrylamide [mole ratio (A)/(B)/(C)=87/5/8];
- terpolymer of stearyl methacrylate, pentacosaethoxylated behenyl methacrylate and N,N-dimethylacrylamide [mole ratio (A)/(B)/(C)=80/5/15];
- terpolymer of stearyl methacrylate, pentacosaethoxylated behenyl methacrylate and N,N-dimethylacrylamide [mole ratio (A)/(B)/(C)=85/10/5];
- terpolymer of stearyl methacrylate, pentacosaethoxylated behenyl methacrylate and N,N-dimethylacrylamide [mole ratio (A)/(B)/(C)=80/10/10];
- terpolymer of stearyl methacrylate, pentacosaethoxylated behenyl methacrylate and N,N-dimethylacrylamide [mole ratio (A)/(B)/(C)=90/5/5]; or
- terpolymer of stearyl methacrylate, pentacosaethoxylated behenyl methacrylate and N,N-dimethylacrylamide [mole ratio (A)/(B)/(C)=95/2.5/2.5].

A subject of the invention is also a process for preparing the copolymer as defined previously, comprising:
- a step a) of preparing an organic phase by mixing, in the desired molar proportions, at least one oil with stearyl methacrylate, the monomer of formula (I) and, where appropriate, the neutral monomer;
- a step b) of polymerization initiated by introducing into the mixture resulting from step a) a thermal initiator to obtain a solution in oil of the expected copolymer; and, if desired
- a step c) of removing the oil from the copolymer solution obtained in step b).

In the process as defined previously, the oil used may be a mineral oil or an oil of plant origin or a mixture of mineral oils and/or of oils of plant origin. The oil or the mixture of oils used in the process that is the subject of the present invention must be liquid at room temperature and more generally in the temperature range between 15° C. and 45° C. or, for certain uses, between 4° C. and 45° C.

In the process as defined previously, the term "mineral oil" especially denotes paraffins, isoparaffins or cycloparaffins having at room temperature a density of between 0.7 and 0.9 and a boiling point of greater than about 150° C., for instance:
- Isopar™ H, Isopar™ G or Isopar™ M,
- Marcol™ 52, which is a commercial oil corresponding to the definition of petroleum jelly oils in the French Codex, and which is a white mineral oil complying with the FDA regulations 21 CFR 172.878 and CFR 178.3620 (a). It is registered in the US Pharmacopeia US XXIII (1995) and in the European Pharmacopeia (1993);
- isohexadecane, identified in Chemical Abstracts by the number RN=4390-04-9, which is a mixture of C12, C16 and C20 isoparaffins containing at least 97% of C16 isoparaffins, among which the main constituent is 2,2,4,4,6,8,8-heptamethyl nonane (RN=4390-04-9);
- isododecane.

In the process as defined previously, the term "plant oil" especially denotes a plant oil of ester or triglyceride type, for instance cocoyl caprylate caprate, for example Dub™ 810C sold by the company Dubois, or jojoba oil.

Step a) of the process as defined previously is performed with stirring until total dissolution of the monomers used is obtained.

Step b) of the process as defined previously is typically performed at a temperature of about 80° C. and left to proceed until polymerization is complete.

In step c) of the process as defined previously, the term "thermal initiator" especially denotes azobis(isobutyronitrile) (AIBN) or lauroyl peroxide.

Step c) of removal of the oil, which is optionally performed in the process as defined previously, is generally performed by prior precipitation of the copolymer formed after step b) with a suitable precipitation solvent, for instance acetone, followed by filtration of the precipitate. The oil may also be removed by atomization of the solution obtained in step b).

A subject of the invention is also the copolymer solution directly obtained after step b) of the process as defined above.

A subject of the invention is also the use of the copolymer as defined previously or of the polymer solution as defined above, as a rheology modifier in a cosmetic, dermopharmaceutical or pharmaceutical topical composition, and more particularly the use as defined above, in which the cosmetic, dermopharmaceutical or pharmaceutical topical composition is an emulsion of water-in-oil type.

A topical composition according to the invention, intended to be applied to the skin, the hair, the scalp or mucous membranes of man or animals, may consist of a topical emulsion comprising at least one aqueous phase and at least one oil phase. This topical emulsion is more particularly of the water-in-oil type. The oil phase of the topical emulsion may consist of a mixture of one or more oils.

A topical composition according to the invention may be intended for cosmetic use or may be used to prepare a medicament for treating skin, scalp and mucous membrane diseases. In the latter case, the topical composition then comprises an active principle which may consist, for example, of an anti-inflammatory agent, a muscle relaxant, an antifungal agent or an antibacterial agent.

When the topical composition is used as a cosmetic composition to be applied to the skin, the scalp or mucous membranes, it may or may not comprise an active principle, for example a moisturizer, a tanning agent, a sunscreen, an antiwrinkle agent, a slimming agent, a free-radical scavenger, an antiacne agent or an antifungal agent.

The topical composition may also comprise compounds conventionally included in compositions of this type, for example fragrances, preserving agents, antioxidants, colorants, emollients or surfactants.

A subject of the invention is also a process for modifying the rheology of a cosmetic, dermopharmaceutical or pharmaceutical topical composition comprising a fatty phase, characterized in that an effective amount of the copolymer as defined previously or of the polymer solution as defined previously is introduced into said fatty phase.

Finally, a subject of the invention is a cosmetic, dermopharmaceutical or pharmaceutical topical composition and more particularly a water-in-oil emulsion according to the invention usually comprising, per 100% of its total mass, between 0.1 mass % and 10 mass % and more particularly between 1 mass % and 5 mass % of the copolymer as defined above.

The examples that follow are intended to illustrate the present invention.

EXAMPLE 1

Copolymers of stearyl Methacrylate and Pentacosaethoxylated Behenyl Methacrylate in Isopar™ H Preparation a)—56.2 g of Isopar™ H are first placed in a reactor. 35.5 g of stearyl methacrylate and 8.3 g of pentacosaethoxylated behenyl methacrylate are then gradually added with stirring, while maintaining the temperature at about 30° C.

b)—After degassing under nitrogen for about 30 minutes, the temperature is raised to 80° C. and polymerization is then initiated by adding 0.5 mol % of azobis(isobutyronitrile). The polymerization is left to proceed for 7 hours and the expected copolymer is obtained as a solution in the oil.

A solution in the oil of the copolymer of stearyl methacrylate and pentacosaethoxylated behenyl methacrylate (mole ratio A/B=95/5), referred to hereinbelow as compound 1A, is obtained.

By varying the molar proportion of indicated monomers, the solutions in oil of the following copolymers are prepared in the same manner:
  copolymer of stearyl methacrylate and pentacosaethoxylated behenyl methacrylate (mole ratio A/B=90/10), referred to hereinbelow as compound 1B;
  copolymer of stearyl methacrylate and pentacosaethoxylated behenyl methacrylate (mole ratio A/B=85/15), referred to hereinbelow as compound 1C;
  copolymer of stearyl methacrylate and pentacosaethoxylated behenyl methacrylate (mole ratio A/B=80/20), referred to hereinbelow as compound 1D.

Evaluation of the Properties

Marcol™ 52 is added to each of the solutions of copolymers 1A to 1D so as to obtain a solution containing 5 mass % of copolymer, which is then made up with 1 mass % of water per 100% of oil phase.

Each of the fatty-phase samples is then placed for 30 seconds in a water bath at 80° C. and then stirred at 500 rpm for about 3 hours. The observations in terms of visual aspect of the copolymer solutions and of consistency of the gels obtained are collated in the table below.

|  | Copolymer | | | |
| --- | --- | --- | --- | --- |
|  | 1A | 1B | 1C | 1D |
| Aspect of the solution in oil | Clear | Clear | Clear | Clear |
| Consistency of the final gel | *** | ** | ** | ** |

Viscosity scale:
* insufficiently viscous,
** viscous,
*** more viscous

EXAMPLE 2

Terpolymers of Stearyl Methacrylate, Pentacosaethoxylated Behenyl Methacrylate and N,N-Dimethylacrylamide in Isopar™ H Preparation a)—56.2 g of Isopar™ H are first placed in a reactor. 34.16 g of stearyl methacrylate, 8.72 g of pentacosaethoxylated behenyl methacrylate and 0.792 g of N,N-dimethylacrylamide are then gradually added with stirring, while maintaining the temperature at about 30° C.

b)—After degassing under nitrogen for about 30 minutes, the temperature is raised to 80° C. and polymerization is then initiated by adding 0.5 mol % of azobis(isobutyronitrile). The polymerization is left to proceed for 7 hours and the expected copolymer is obtained as a solution in the oil.

A solution in the oil of the terpolymer of stearyl methacrylate, pentacosaethoxylated behenyl methacrylate and N,N-dimethylacrylamide (mole ratio A/B=87/5/8), referred to hereinbelow as compound 2A, is obtained.

By varying the molar proportion of indicated monomers, the solutions in oil of the following copolymers are prepared in the same manner:
  terpolymer of stearyl methacrylate, pentacosaethoxylated behenyl methacrylate and N,N-dimethylacrylamide (mole ratio A/B/C=80/5/15), referred to hereinbelow as compound 2B;
  terpolymer of stearyl methacrylate, pentacosaethoxylated behenyl methacrylate and N,N-dimethylacrylamide (mole ratio A/B/C=85/10/5), referred to hereinbelow as compound 2C;
  terpolymer of stearyl methacrylate, pentacosaethoxylated behenyl methacrylate and N,N-dimethylacrylamide (mole ratio A/B/C=80/10/10), referred to hereinbelow as compound 2D;
  terpolymer of stearyl methacrylate, pentacosaethoxylated behenyl methacrylate and N,N-dimethylacrylamide (mole ratio A/B/C=90/5/5), referred to hereinbelow as compound 2E;
  terpolymer of stearyl methacrylate, pentacosaethoxylated behenyl methacrylate and N,N-dimethylacrylamide (mole ratio A/B/C=95/2.5/2.5) referred to hereinbelow as compound 2F.

Evaluation of the Properties

Marcol™ 52 is added to each of the solutions of copolymers 2A to 2F so as to obtain a solution containing 5 mass % of copolymer, which is then made up with 1 mass % of water per 100% of oil phase.

Each of the fatty-phase samples is then placed for 30 seconds in a water bath at 80° C. and then kept stirring at 500 rpm for about 3 hours. The observations in terms of visual aspect of the copolymer solutions and of consistency of the gels obtained are collated in the table below.

|  | Copolymer | | | | | |
|---|---|---|---|---|---|---|
|  | 2A | 2B | 2C | 2D | 2E | 2F |
| Aspect of the solution in oil | Clear | Clear | Clear | Clear | Clear | Clear |
| Consistency of the final gel | **** | **** | ** | ** | **** | ** |

Viscosity scale:
* insufficiently viscous,
** viscous,
*** more viscous

Comparative Example

Copolymer of Stearyl Methacrylate and
N,N-Dimethylacrylamide in Isopar™ H

Preparation a)—56.2 g of Isopar™ H are first placed in a reactor. 41.6 g of stearyl methacrylate and 1.1 g of N,N-dimethylacrylamide are then gradually added with stirring, while maintaining the temperature at about 30° C.

b)—After degassing under nitrogen for about 30 minutes, the temperature is raised to 80° C. and polymerization is then initiated by adding 0.5 mol % of azobis(isobutyronitrile). The polymerization is left to proceed for 7 hours and the expected copolymer as a solution in the oil is obtained.

A solution in the oil of the copolymer of stearyl methacrylate and N,N-dimethylacrylamide (mole ratio A/B=85/15), referred to hereinbelow as compound C, is obtained.

Evaluation of the Properties

Marcol™ 52 is added to the solution of copolymer C so as to obtain a solution containing 5 mass % of copolymer, which is then made up with 1 mass % of water per 100% of oil phase.

The fatty-phase sample is then placed for 30 seconds in a water bath at 80° C. and then kept stirring at 500 rpm for about 3 hours. The observations in terms of visual aspect of the copolymer solution and of consistency of the gel obtained are collated in the table below.

|  | Copolymer C |
|---|---|
| Aspect of the solution in oil | Clear |
| Consistency of the final gel | * |

Viscosity scale:
* insufficiently viscous

These tests demonstrate that the copolymers according to the invention are good oil thickeners insofar as they modify their rheology while requiring a minimum amount of water, in contrast with the prior-art polymers, thus making it possible readily to obtain clear gels.

The comparison with copolymer C of the comparative example also demonstrates that the presence in the copolymers according to the invention of monomer units derived from the compound of formula (I) is essential.

The invention claimed is:

1. A copolymer consisting of, per 100 mol %:
    a) more than 70 mol % and up to 99.9 mol % of hydrophobic monomer units (A) derived from stearyl methacrylate; and
    b) from 0.1 mol % to 30 mol % of monomer units (B) derived from at least one monomer of a compound of formula (I):

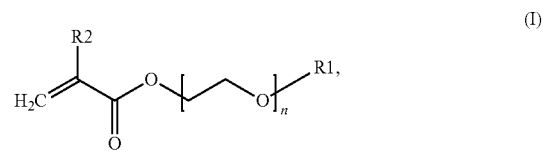

(I)

in which R1 represents a linear or branched alkyl radical comprising from 12 to 22 carbon atoms, R2 represents a hydrogen atom or a methyl radical and n is an integer greater than or equal to 0 and less than or equal to 30, wherein said compound of formula (I) is not stearyl methacrylate.

2. The copolymer as defined in claim 1, wherein, in formula (I), the radical R1 represents a linear alkyl radical chosen from dodecyl and docosanyl radicals.

3. The copolymer as defined in claim 1, wherein, in formula (I), n is greater than zero and more particularly n is greater than or equal to four and less than or equal to twenty five.

4. The copolymer as defined in claim 3, wherein the copolymer is the copolymer of stearyl methacrylate and pentacosaethoxylated behenyl methacrylate or the copolymer of stearyl methacrylate and tetraethoxylated lauryl acrylate.

5. The copolymer as defined in claim 4, wherein the copolymer is selected from the group consisting of:
    copolymer of stearyl methacrylate and of pentacosaethoxylated behenyl methacrylate having a mole ratio (A)/(B)=95/5,
    copolymer of stearyl methacrylate and pentacosaethoxylated behenyl methacrylate having a mole ratio (A)/(B)=90/10,
    copolymer of stearyl methacrylate and pentacosaethoxylated behenyl methacrylate having a mole ratio (A)/(B)=85/15, and
    copolymer of stearyl methacrylate and pentacosaethoxylated behenyl methacrylate having a mole ratio (A)/(B)=80/20.

6. The copolymer as defined in claim 1, wherein the mole ratio (A)/(B) is between 80/20 and 95/5.

* * * * *